Figure 1:
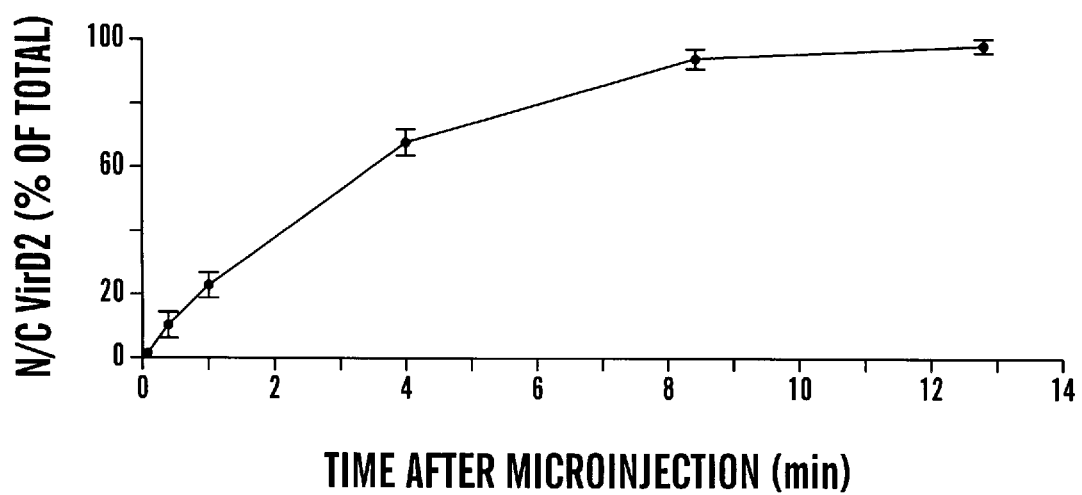

United States Patent [19]
Citovsky

[11] Patent Number: 5,831,020
[45] Date of Patent: Nov. 3, 1998

[54] PROTEIN-MEDIATED NUCLEAR IMPORT OF DNA

[75] Inventor: Vitaly H. Citovsky, Commack, N.Y.

[73] Assignee: The Research Foundation of State University of New York, Albany, N.Y.

[21] Appl. No.: 824,151

[22] Filed: Mar. 25, 1997

Related U.S. Application Data

[60] Provisional application No. 60/014,055, Mar. 25, 1996.

[51] Int. Cl.$^6$ ................................................. C07K 14/195
[52] U.S. Cl. ................................................................ 530/350
[58] Field of Search ..................................... 530/300, 350

[56] References Cited

PUBLICATIONS

Guralnick et al. Transport of DNA into the nuclei of Xenopus oocytes by a modified VirE2 protein of Agrobacterium. The Plant Cell vol. 8 pp. 363–373, 1996.
Bukrinsky, M.I., et al., Proc Natl Acad Sci USA 89:6580–6584(1992).
Bukrinsky, M.I., et al., Nature 365:666–669(1993).
Citovsky, V., et al., Science 256(5065):1802–1805(Jun. 26, 1992).
Citovsky, V., and Zambryski, P., Annu Rev Microbiol 47:167–197(1993).
Citovsky, V., et al., Proc Natl Acad Sci USA 91(8):3210–3214(Apr. 12, 1994).
Citovsky, V., and Zambryski, P., Membr Prot Transport 1:39–57(1995).
Clever, J., et al., Proc Natl Acad Sci USA 88:7333–7337(1991).
Dowty, M.E., et al., Proc Natl Acad Sci USA 92:4572–4576(1995).
Escudero, J., et al., Proc Natl Acad Sci USA 92:230–234(1995).
Finlay, D.R., et al., J Cell Biol 104:189–200(1987).
Fullner, K.J., et al., Mol Gen Genet 245(6):704–715(Dec. 15, 1994).
Herrera–Estrella, A., et al., Proc Natl Acad Sci USA 87(24):9534–9537(Dec. 1990).
Herrera–Estrella, A., et al., EMBO J 7:4055–4062(1988).
Howard, E.A., et al., Cell 68(1):109–118(Jan. 10, 1992).
Howard, E.A., and Citovsky, V., BioEssays 12:103–108(1990).
Howard, E.A., et al., UCLA Symp Mol Cell Biol New Ser 129:1–11(1990).
Jasper, F. et al., Proc Natl Acad Sci USA 91(2):694–698(Jan. 18, 1994).
Kaneda, Y., et al., Science 243:375–378(1989).
Koukolikova–Nicola, Z., et al., J Bacteriol 175(3):723–731(Feb. 1993).
Rossi, L., et al., Mol Gen Genet 239(3):345–353(Jun. 1993).
Shurvinton, C.E., et al., Proc Natl Acad Sci USA 89(24):11837–11841(Dec. 15, 1992).
Tinland, B., et al., EMBO J 14(14):3585–3595(Jul. 17, 1995).
Tinland, B. et al., Proc Natl Acad Sci USA 89(16):7442–7446(Aug. 15, 1992).
von Schwedler, U., et al., Proc Natl Acad Sci USA 91:6992–6996(1994).
Zupan, J.R., and Zambryski, P., Plant Physiol 107:1041–1047(1995).

*Primary Examiner*—George C. Elliott
*Assistant Examiner*—John S. Brusca
*Attorney, Agent, or Firm*—Jaeckle Fleischmann & Mugel, LLP; Susan J. Braman, Esq.

[57] ABSTRACT

The invention provides a nuclear targeting molecule having a nucleic acid sequence which encodes a nuclear localization signal of a VirE2 protein of Agrobacterium, the nuclear localization signal of the VirE2 protein having a mutation therein which renders the nuclear localization signal of the VirE2 protein capable of targeting deoxyribonucleic acid into the nucleus of an animal cell. The invention further provides a plasmid for targeting a DNA molecule into the nucleus of a host cell. The plasmid comprises the nuclear targeting molecule and a DNA molecule to be targeted to a nucleus. This plasmid of the subject invention can be introduced into various host cells, and the nuclear targeting molecule will target the DNA molecule to the nucleus of the host cell. Thus, the invention further provides a method of targeting a DNA molecule into the nucleus of a host cell. A purified nuclear targeting peptide of a VirE2 protein of Agrobacterium is also provided, the nuclear targeting peptide of the VirE2 protein having a mutation therein which renders the nuclear targeting peptide of the VirE2 protein capable of targeting deoxyribonucleic acid into the nucleus of an animal cell.

1 Claim, 1 Drawing Sheet

PROTEIN-MEDIATED NUCLEAR IMPORT OF DNA

This application claims priority of U.S. provisional patent application Ser. No. 60/014,055, filed Mar. 25, 1996.

The subject invention was made with support under Grant No. RO1-GM50224 of the National Institutes of Health, Grant No. 94-02564 of the U.S. Department of Agriculture, and Grant No. US-2247-93 of the U.S.-Israel Binational Agricultural Research & Development Fund.

FIELD OF INVENTION

The subject invention is directed to a molecule/protein and method for importing DNA into the nucleus of a cell, and more particularly to a nuclear targeting molecule/peptide which can be used to target a DNA molecule to the nucleus of a host cell.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Intracellular macromolecular (i.e. protein) transport into and out of the nucleus occurs through the nuclear pore complex (NPC) (for recent reviews see Hicks and Raikhel 1995; Melchoir and Gerace 1995). It has recently been shown that certain ribonucleic acids (RNAs) including several of the U small nuclear ribonucleoproteins (snRNPs) appear to use the same pathway for their import into the nucleus (Hamm et al. 1990; Michaud and Goldfarb 1991; Michaud and Goldfarb 1992; O'Neill et al. 1995). This type of pathway has been proposed to occur in the nuclear import of Influenza A RNAs.

In contrast to what is known about protein and snRNP nuclear entry, the mechanism of entry of exogenous deoxyribonucleic acid (DNA) into the nucleus is largely unknown. All studies involving recombinant eukaryotic gene expression rely on the ability of the introduced gene to become nuclear to function, regardless of how the DNA is introduced into the cell. Nuclear localization of extrachromosomal DNA is also important in a number of viral life cycles (Fields et al. 1990). While the nuclear import of exogenous DNA has been addressed in several experimental systems, including that of the single stranded Ti-DNA from *Agrobacterium tumefaciens* in tobacco (Escudero et al. 1995; Zupan and Zambryski 1995) and of the human immunodeficiency virus (HIV) pre-integration complex (PIC) in quiescent T cells (Bukrinsky et al. 1992; Bukrinsky et al. 1993; von Schwedler et al. 1994), no general mechanisms have been elucidated. The nuclear import of HIV PICs appears to depend on the presence of a functional NTS within the matrix protein which is present in the PIC (Bukrinsky et al. 1992; Bukrinsky et al. 1993; von Schwedler et al. 1994).

It has recently been shown that plasmid DNA injected into multinucleated rat myotubes becomes nuclear within 10 to 20 hours as assayed by β-galactosidase activity expressed from the lacZ gene encoded in the injected plasmids (Dowty et al. 1995). This expression was inhibited by wheat germ agglutinin (WGA), suggesting import through the NPC (Finlay et al. 1987). However, when the DNA was labeled with biotin and injected into the cells, no nuclear DNA was detected. Similarly, only small numbers of colloidal gold particles, representing gold-labeled DNA, could be detected in the nuclei of a few of the injected cells. Additionally, gene expression was unaffected by energy depletion, further complicating the role of the NPC and the nuclear "import".

An intrinsic problem to many of these experiments is that gene expression is a measure not only of DNA nuclear localization, but also of transcription factor nuclear import, transcription, messenger RNA (mRNA) processing and export, and translation. Thus, the effects of agents that alter any of these processes could be misinterpreted as directly modulating DNA import.

Agrobacterium is a phytopathogen that elicits neoplastic growths on many plant species. This genetic transformation of plants is achieved by transferring a single-stranded copy of the bacterial T-DNA (the T-strand) from the Ti plasmid into the plant cell nucleus (Tinland et al. 1994; Yusibov et al. 1994; Citovsky and Zambryski 1995). Nuclear import of the T-strand is likely mediated by two Agrobacterium proteins, VirD2 and VirE2 (reviewed by Citovsky and Zambryski 1993; Citovsky and Zambryski 1995). Presumably, both proteins directly associate with the transported T-strand to form the T-complex (Howard and Citovsky 1990; Howard et al. 1990). In this complex, one molecule of VirD2 is covalently attached to the 5' end of the T-strand (Herrera-Estrella et al. 1988; Ward and Barnes 1988; Young and Nester 1988; Howard et al. 1989) while VirE2, a single stranded (ss) DNA binding protein (SSB) (Gietl et al. 1987; Christie et al. 1988; Citovsky et al. 1988; Citovsky et al. 1989), is thought to cooperatively coat the rest of the ssDNA molecule (Citovsky et al. 1989). Recent studies demonstrated that VirD2 and VirE2 are karyophilic, presumably acting to transport the associated T-strand into the plant cell nucleus (Herrera-Estrella et al. 1988; Citovsky et al. 1992b; Howard et al. 1992; Citovsky et al. 1994). The nuclear localization signal (NLS) sequences of VirD2 and VirE2 have been identified and characterized in detail; specifically, VirD2 has been shown to contain one bipartite NLS (Howard et al. 1992) and VirE2 two independently-active bipartite NLSs (Citovsky et al. 1992b). VirD2 and VirE2 NLSs function in various plant species; furthermore, the NLSs of both proteins are active even in plants recalcitrant to Agrobacterium infection (Citovsky et al. 1994), indicating the universal character of these signals in plants.

The T-DNA element itself presumably does not carry signals for nuclear transport because it is sequence non-specific; any DNA placed between the T-DNA borders of the Ti plasmid will be transported into the plant cell nucleus and function as the T-DNA (reviewed by Zambryski 1992). Thus, the VirD2 and VirE2 NLSs are likely the only signals required for the T-DNA nuclear import. This role of VirD2 and VirE2 in the T-DNA nuclear uptake, however, was inferred from their proposed association with the transported DNA (Citovsky et al. 1992b; Howard et al. 1992) and has not been demonstrated directly. In fact, the hypothesis that a specific protein can physically transport DNA into the cell nucleus has not been proven. A few studies implicating proteins in DNA nuclear import employed either non-specific nuclear proteins (Kaneda et al. 1989) or the entire particles of the SV40 virus (Clever et al. 1991). In contrast, the T-DNA nuclear import is a simple and well-defined experimental system to study protein-mediated transport of DNA molecules across the nuclear envelope.

The success of many proposed gene therapy techniques will likely rely on the ability to import exogenous DNA into the nucleus of a host cell. A need exists, therefore, for the elucidation of a mechanism for successfully importing such exogenous DNA.

SUMMARY OF THE INVENTION

This need is met by the nuclear targeting molecule/peptide and method of the subject invention. More particularly, the invention provides a nuclear targeting molecule having a nucleic acid sequence which encodes a nuclear localization signal of a VirE2 protein of Agrobacterium, the nuclear localization signal of the VirE2 protein having a mutation therein which renders the nuclear localization signal of the VirE2 protein capable of targeting deoxyribonucleic acid into the nucleus of an animal cell. The invention further provides a plasmid for targeting a DNA molecule into the nucleus of a host cell. The plasmid comprises the nuclear targeting molecule and a DNA molecule to be targeted to a nucleus. This plasmid of the subject invention can be introduced into various host cells, and the nuclear targeting molecule will target the DNA molecule to the nucleus of the host cell.

Thus, the invention further provides a method of targeting a DNA molecule into the nucleus of a host cell. The method comprises providing a plasmid (the plasmid comprising the nuclear targeting molecule and the DNA molecule to be targeted) and introducing the plasmid into the cytoplasm of the host cell. In this method, the nuclear targeting molecule targets the DNA molecule into the nucleus of the host cell.

Further provided is a purified nuclear targeting peptide of a VirE2 protein of Agrobacterium, the nuclear targeting peptide of the VirE2 protein having a mutation therein which renders the nuclear targeting peptide of the VirE2 protein capable of targeting deoxyribonucleic acid into the nucleus of an animal cell.

More particularly, Agrobacterium T-DNA nuclear transport was used to examine (i) the specificity of nuclear targeting between plants and animals, and (ii) the nuclear import of DNA by a specialized transport protein. Two karyophilic Agrobacterium proteins, VirD2 and VirE2, which presumably associate with the transported T-DNA and function in many plant species, were microinjected into Drosophila embryos and Xenopus oocytes. In both animal systems, VirD2 localized to the cell nuclei and VirE2 remained exclusively cytoplasmic, suggesting that VirE2 nuclear localization signals (NLSs) may be plant-specific. Repositioning one amino acid residue within VirE2 NLSs enabled them to function in animal cells. The modified VirE2 protein bound DNA and actively transported it into the nuclei of Xenopus oocytes. These observations suggest the functional difference in nuclear import between animals and plants and show that DNA can be transported into the cell nucleus via a protein-specific pathway.

BRIEF DESCRIPTION OF THE FIGURE

These and other features and advantages of this invention will be evident from the following detailed description of preferred embodiments when read in conjunction with the accompanying drawing in which:

FIG. 1 illustrates the kinetics of VirD2 nuclear import. Drosophila embryos were microinjected with the fluorescently-labeled VirD2 and the intracellular fluorescence was recorded using time-lapse video. The intensity of intranuclear and cytoplasmic fluorescence was quantified using images recorded at the indicated time points and the degree of VirD2 nuclear import was expressed as a ratio between the nuclear and cytoplasmic fluorescence. Each point of the curve represents the average of twenty different nuclei.

DETAILED DESCRIPTION OF THE INVENTION

The subject invention thus provides a nuclear targeting molecule having a nucleic acid sequence which encodes a nuclear localization signal of a VirE2 protein of Agrobacterium, the nuclear localization signal of the VirE2 protein having a mutation therein which renders the nuclear localization signal of the VirE2 protein capable of targeting deoxyribonucleic acid into the nucleus of an animal cell. In one presently preferred embodiment, the mutation comprises one or more amino acid subsitutions in the nuclear localization signal having SEQ ID NO:1. More particularly, the mutated nuclear localization signal of a VirE2 protein is designated VirE2s11 and the one or more substitutions comprise a substitution of arginine for leucine and leucine for arginine to produce SEQ ID NO:2. In another presently preferred embodiment, the mutation comprises one or more amino acid substitutions in the nuclear localization signal having SEQ ID NO:3. More particularly, the mutated nuclear localization signal of a VirE2 protein is designated VirE2s20 and the one or more substitutions comprise a substitution of threonine for lysine and lysine for threonine to produce SEQ ID NO:4.

The nuclear targeting molecule is a DNA molecule, and can be isolated from Agrobacterium and then mutated, or synthetically constructed based on the desired nucleotide and/or amino acid sequence. As used herein, the term "isolated" when used in conjunction with Agrobacterium refers to a nucleic acid sequence separated from the entire Agrobacterium genome or from another vector which includes the desired portion of the Agrobacterium genome.

The entire nucleotide and amino acid sequences of the VirE2 protein of Agrobacterium have been published by Hirooka et al. 1987, and the amino acid sequence of the NLSs of VirE2 have been published by Citovsky et al. 1992b. The contents of these references are hereby incorporated by reference to more fully describe the state of the art to which the subject invention pertains.

The nuclear targeting molecule is most readily used by providing a plasmid (an extrachromosomal piece of DNA) for targeting a DNA molecule into a nucleus of a host cell. The plasmid, in its most basic form, comprises a nuclear targeting molecule having a nucleic acid sequence as described above, and a DNA molecule to be targeted to a nucleus of a host cell. The structural connection of the two parts of the plasmid are that the two are contained on the same plasmid. Since the DNA molecule to be targeted need not be under expressional control of the nuclear targeting molecule (see below), the DNA molecule does not need to be "downstream" of the nuclear targeting molecule. As should be readily understood by those skilled in the art, "upstream" and "downstream" refer to location in the plasmid relative to the orientation of a gene (the DNA molecule to be targeted). For example, if a gene is presented in a 5' to 3' orientation, sequences to the 5' region of the gene are "upstream" and sequences to the 3' region of the gene are "downstream". In the case of a circular DNA molecule, upstream and downstream are given meaning in relation to the orientation of a given gene. The nuclear targeting protein is used by complexing the protein with the DNA molecule to be targeted, or by providing a plasmid which comprises a nucleic acid sequence encoding the nuclear targeting protein and a DNA molecule to be targeted.

The DNA molecule to be targeted to the nucleus generally encodes a protein or enzyme which would be desirable to express in the nucleus of a cell, and generally is exogenous DNA (i.e., such an encoded protein or enzyme is not being expressed in the host cell or is being expressed at very low levels). Many examples of DNA molecules for which it would be desirable to import the molecules into a host cell should be readily apparent to those skilled in the art. For example, many proposed gene therapy techniques would benefit from the ability to import a DNA molecule into the nucleus according to the subject invention. Recently, numerous examples of DNA molecules which could be imported according to the subject invention has been published. The following are examples, for illustration only, of suitable DNA molecules. Vrionis et al. 1995 disclose that the expression of herpes simplex virus thymidine kinase (HSV-tk) in a host cell may be useful in the treatment and/or prevention of brain tumors. Knowles et al. 1995 disclose that the expression of the cystic fibrosis transmembrane conductance regulator in pulmonary epithelia may be useful in the treatment and/or prevention of cystic fibrosis lung disease. Rowland et al. 1995 disclose that the expression of missing or defective proteins may be useful in the treatment and/or prevention of cardiovascular disease. Baru et al. 1995 disclose that the expression of clotting factor IX may be useful in the treatment and/or prevention of hemophilia B. Brownlee 1995 disclose that the expression of clotting factor VIII may be useful in the treatment and/or prevention of hemophilia A. Osborne et al. 1995 disclose that the expression of erythropoietin may be useful in the treatment of anemia associated with chronic renal failure, cancer, and HIV infections. Kojima et al. 1995 disclose that the expression of brain-derived neurotrophic factor may be useful in the treatment and/or prevention of neurodegenerative diseases. Betz et al. 1995 disclose that the expression of interleukin-1 receptor antagonist protein (IL-1ra) may be useful in the reduction of ischemic brain injury damage. Vaulont et al. 1995 disclose that the expression of adenosine deaminase may be useful in the treatment and/or prevention of an autosomal recessive form of severe combined immunodeficiency (SCID). Ekhterae and Stanley 1995 disclose that the expression of tissue plasminogen activator (tPA) may be useful in the enhancement of fibrinolytic activity of vascular cells. Stevenson et al. 1995 disclose that the expression of apolipoprotein E (apo E) may be useful in the treatment and/or prevention of hyperlipidemias. Phaneuf et al. 1995 disclose that the expression of fumarylacetoacetate hydrolase (FAH) may be useful in the treatment and/or prevention of type 1 hereditary tyrosinemia. Each of the above references provides a separate example of the applicability of the subject invention to nuclear importation of many different DNA molecules, for many different reasons. As should be readily apparent from the above examples, many applications of the method of the subject invention could be in the area of gene therapy, where a protein or enzyme of interest can be imported into the nucleus of the desired host cell.

The plasmid of the subject invention may contain other elements in addition to the nuclear targeting molecule or protein and the DNA molecule to be targeted. For example, it may be desirable to include a bacterial origin of replication (such as ori C for replication in *Escherichia coli*, or the origin of replication of *Bacillus subtilis* for replication therein, or the origin of replication of *Pseudomonas aeruginosa* for replication therein, etc.) so that the plasmid can be maintained and replicated in a bacterial host. Such an embodiment of the plasmid of the subject invention could also include a selection marker for selecting bacterial colonies which contain the subject plasmid. Such selection or biological markers are well known in the art. In bacteria, these are commonly drug-resistance genes. Drug or antibiotic resistance is used to select bacteria that have taken up cloned DNA from the much larger population of bacteria that have not.

A selection marker can also be included in the plasmid to identify mammalian cells which have taken up the plasmid DNA. In the early mammalian gene transfer experiments involving viral genes, the transfer of exogenous DNA into cells was detected because the DNA had a biological activity; it led to production of infectious virus or produced stable changes in the growth properties of the transfected cells. The herpes simplex virus thymidine kinase (HSV tk) gene can be used as a selectable genetic marker in mammalian cells in much the same way that drug-resistance genes work in bacteria, to allow rare transfected cells to grow up out of a much larger population that did not take up any DNA. The cells are transferred to selective growth medium, which permits growth only of cells that took up a functional tk gene (and the transferred DNA of interest). Various dominant selectable markers are now known in the art, including:

aminoglycoside phosphotransferase (APH), using the drug G418 for selection which inhibits protein synthesis; the APH inactivates G418;

dihydrofolate reductase (DHFR):Mtx-resistant variant, using the drug methotrexate (Mtx) for selection which inhibits DHFR; the variant DHFR is resistant to Mtx;

hygromycin-B-phosphotransferase (HPH), using the drug hygromycin-B which inhibits protein synthesis; the HPH inactivates hygromycin B;

thymidine kinase (TK), using the drug aminopterin which inhibits de nova purine and thymidylate synthesis; the TK synthesizes thymidylate;

xanthine-guanine phosphoribosyltransferase (XGPRT), using the drug mycophenolic acid which inhibits de novo GMP synthesis; XGPRT synthesizes GMP from xanthine; and adenosine deaminase (ADA), using the drug 9-β-D-xylofuranosyl adenine (Xyl-A) which damages DNA; the ADA inactivates Xyl-A.

Gene amplification can also be used to obtain very high levels of expression of transfected gene. When cell cultures are treated with Mtx, an inhibitor of a critical metabolic enzyme, DHFR, most cells die, but eventually some Mtx-resistant cells grow up. A gene to be expressed in cells is cotransfected with a cloned dhfr gene, and the transfected cells are subjected to selection with a low concentration of Mtx. Resistant cells that have taken up the dhfr gene (and, in most cases, the cotransfected gene) multiply. Increasing the concentration of Mtx in the growth medium in small steps generates populations of cells that have progressively amplified the dhfr gene, together with linked DNA. Although this process takes several months, the resulting cell cultures capable of growing in the highest Mtx concentrations will have stably amplified the DNA encompassing the dhfr gene a hundredfold or more, leading to significant elevation of the expression of the cotransfected gene.

It may also be desirable to include, as an element of the plasmid according to the subject invention, a molecule encoding a promoter to control expression of the DNA molecule to be targeted. Such a promoter sequence would need to be positioned upstream from the DNA molecule to effectively control expression of the DNA molecule. RNA polymerase normally binds to the promoter and initiates transcription of a gene (the DNA molecule) or a group of linked genes and regulatory elements (operon). Promoters vary in their strength, i.e., ability to promote transcription. For the purpose of expressing the DNA molecule of the invention, it is desirable to use strong promoters in order to obtain a high level of transcription and, hence, expression of the gene. Depending upon the host cell system utilized, any one of a number of suitable promoters can be used, such as, the lac promoter, trp promoter, recA promoter, ribosomal RNA promoter, the $P_R$ and $P_L$ promoters of coliphage lambda, and others, including but not limited to, lacUV5, ompF, bla, lpp and the like, nos promoter, the small subunit ribulose bisphosphate carboxylase genes, the small subunit chlorophyll A/B binding polypeptide, the 35S promoter of cauliflower mosaic virus, and promoters isolated from plant genes, including the Pto promoter itself (Vallejos et al. 1986) to direct high levels of transcription of adjacent DNA segments. Additionally, a hybrid trp-lacUV5 (tac) promoter or other *E. coli* promoters produced by recombinant DNA or other synthetic DNA techniques can be used to provide for transcription of the DNA molecule of the invention.

Bacterial host cell strains and expression vectors can be chosen which inhibit the action of the promoter unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the $P_L$ promoter of lambda can be induced by an increase in temperature in host cells containing a temperature sensitive lambda repressor, e.g., c1857. In this way, greater than 95% of the promoter-directed transcription may be inhibited in uninduced cells. Thus, expression of the DNA molecule of the invention can be controlled.

When cloning in a eucaryotic host cell, enhancer sequences (e.g., the 72 bp tandem repeat of SV40 DNA or the retroviral long terminal repeats of LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have the remarkable ability to function upstream from, within, or downstream from eucaryotic genes. Therefore, the position of the enhancer sequence with respect to the inserted gene is less critical.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosomal binding site. Thus, any SD-ATG combination that can be utilized by host cell ribosomes can be employed. Such combinations include but are not limited to the SD-ATG combination from the CRO gene or the N gene of coliphage lambda, or from the *E. coli* tryptophan E, D, C, B or A genes. Additionally, any SD-ATG combination produced by recombinant DNA or other techniques involving incorporation of synthetic nucleotides can be used.

In accordance with the subject invention, the DNA of the plasmid as described herein is targeted into the nucleus of a host cell, where the DNA molecule to be targeted is expressed. Since the nuclear-localized plasmid DNA will eventually be degraded, it may be desirable for long term expression of the DNA molecule in the nucleus of the host cell to integrate the plasmid DNA into the genome of the host cell. In such an embodiment, the plasmid of the subject invention further includes a molecule to direct integration of the DNA molecule into the genome of the host cell. Such integration sequences are known in the art, and include, for example, the inverted terminal repeats of adeno-associated virus (ITRs), retroviral long terminal repeats (LTRs), and other viral sequences shown to cause incorporation or integration of the viral genome into the host cell genome. For integration into plant genomes, the left and right Agrobacterium T-DNA border sequences allow the integration of exogenous DNA located between the left and right T-DNA border sequences into a plant cell.

As should be readily apparent, various additional elements can be included in the plasmid of the subject invention depending upon the desired goal. For ease in constructing various embodiments of the plasmid, the basic plasmid (comprising the nuclear targeting molecule or protein and the DNA molecule to be targeted) can also contain a number of unique restriction enzyme sites for insertion of the additional molecules or elements. As used herein, a "unique" restriction enzyme site refers to the presence of only one cleavage site for a particular restriction endonuclease within the plasmid DNA. That particular restriction endonuclease (or restriction enzyme) will, therefore, only cleave the DNA of the plasmid at that one location or "unique" site. These unique restriction sites can be provided in the plasmid of the subject invention by including a polylinker as an element of the plasmid. As used herein, a "polylinker" refers to a sequence which contains many restriction enzyme recognition sequences that are present only once in the vector or plasmid, i.e., unique restriction sites.

Having constructed the plasmid according to the subject invention, a host cell comprising the plasmid is also provided by the subject invention. As indicated above, for maintenance and propagation of the plasmid, a bacterial host cell (such as *Escherichia coli*) may be used. Bacterial host cells for maintenance and propagation offer the advantages of being easy to work with and capable of rapid reproduction and therefore propagation of the plasmid.

In use however, the DNA molecule to be targeted to the nucleus of a host cell is most likely to express a product useful in animal, mammalian, plant, or insect host cells. Suitable host cells are any cells into which a DNA molecule is desired to be introduced. For example, and referring to the many possible uses of the subject invention discussed above, the host cell may be a pulmonary epithelial cell where gene therapy of cystic fibrosis lung disease is being treated and/or prevented. Vascular cells may be a suitable host cell where tPA is desired to be expressed. Plant cells, such as of various crop plants including potato, tomato, cereals, etc., may be suitable host cells where plant disease resistance genes are desired to be expressed. In a particular insect cell, it may be desirable to express an insecticide resistance gene in order to select for that insect after exposing an environment to the insecticide. Many other suitable host cells should be readily apparent, as the invention has broad applicability to various host cells and various DNA molecules to be imported into the nucleus thereof. The importation of DNA into the nucleus of a host cell may also be desirable in vitro, using various cells lines known in the art, such as, for example, the mammalian cells identified as NIH3T3 cells, Hela cells, COS cells, and CHO cells, and the insect cell lines identified as Drosophila Schneider, Drosophila $K_C$, and Sf9.

A viral vector may provide the means for introducing the plasmid into the host cell. For example, the plasmid may be introduced into an adenovirus or retrovirus vector and these viral vectors can then infect a mammalian cell in order to get the plasmid DNA into the cytoplasm and/or nucleus of the mammalian cell. Other mammalian viruses could similarly be used. The plasmid could also be introduced into an insect virus, such as baculovirus, for introduction into an insect cell, or a plant virus for introduction into a plant cell.

Having thus described the nuclear targeting molecule/ protein and plasmid according to the subject invention, as well as suitable host cells into which the plasmid can be introduced, the invention further provides a method of targeting a DNA molecule into the nucleus of a host cell. The method comprises first providing a plasmid according to the subject invention, and then introducing the plasmid into the cytoplasm of the host cell (see above for description of the plasmid and the host cell). The nuclear targeting molecule which is an element of the plasmid targets the DNA molecule which is another element of the plasmid to the nucleus of the host cell. Alternatively, the nuclear targeting protein of the invention can be complexed with a DNA molecule to be targeted, and the complex can be introduced into a host cell.

Various methods are known in the art for introducing nucleic acid molecules into host cells. One method is microinjection, in which DNA is injected directly into the cytoplasm of cells through fine glass needles. Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller (1989). Various viral vectors have also been used to transform mammalian cells, such as bacteriophage, vaccinia virus, adenovirus, and retrovirus.

As indicated, the method of the subject invention requires the use of a plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in procaryotic and eucaryotic cells. The DNA sequences are cloned into the plasmid vector using standard cloning procedures known in the art, as described by Sambrook et al. (1989).

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

If the plasmid is to be introduced into plant cells, the methods of introduction may differ slightly. The plasmid can be introduced into *Agrobacterium tumefaciens*. This introduction can be accomplished using methods known to those in the art, including electroporation, or particle bombardment. Another method that can be used to introduce the plasmid into *Agrobacterium tumefaciens* is triparental mating. In a triparental mating, the *Escherichia coli* containing the plasmid, a second *Escherichia coli* containing a helper plasmid, and an Agrobacterium are combined, resulting in introduction of the plasmid DNA into the Agrobacterium. The Agrobacterium cells are then screened using a selection marker for the presence of the plasmid DNA therein. Those cells containing the plasmid DNA are then used for further experiments.

The plasmid can also be introduced into a plant cell. One method for introduction of the plasmid into a plant cell is Agrobacterium-mediated transformation of the plant cell (stable or transient). Briefly, the tissue of plants is contacted with an inoculum of the Agrobacterium transformed with the plasmid (with exogenous DNA therein). Generally, this procedure involves inoculating the plant tissue with a suspension of the bacteria and incubating the tissue for 48 to 72 hours on regeneration medium without antibiotics at 25°–28° C.

In practice, the method of Agrobacterium-mediated transformation can involve a three-step process. The plasmid DNA is first analyzed in an *Escherichia coli* host cell, and is then introduced into an *Agrobacterium tumefaciens* host cell, which is then used for Agrobacterium-mediated transfer of the T-DNA within the plasmid to the plant cell. Generally, only a portion of the T-DNA border sequences and DNA located therebetween is transferred into the plant cell by such Agrobacterium-mediated transfer. Therefore, any exogenous DNA for transfer into the plant cell should be located within the plasmid between the T-DNA border sequences.

The leaf disk technique can be utilized in conjunction with Agrobacterium-mediated transformation. Briefly, wounded plant cells (such as leaves, roots and stems) are cultured briefly with Agrobacterium cells to initiate transfer of the T-DNA from the Agrobacterium to the plant cell. After several days, the plant tissue is transferred to shoot-inducing media that contains a selective agent. After shoots are formed, the shoots are transferred to a medium that stimulates root formation.

Another method for introduction of the plasmid into a plant cell is by transformation of the plant cell cytoplasm, such as by particle bombardment.

A further method for introduction of the plasmid into a plant cell is by transformation of plant cell protoplasts (stable or transient). Plant protoplasts are enclosed only by a plasma membrane and will therefore take up macromolecules like exogenous DNA. These engineered protoplasts can be capable of regenerating whole plants. Suitable methods for introducing exogenous DNA into plant cell protoplasts include electroporation and polyethylene glycol (PEG) transformation.

An additional method for introduction of the plasmid into a plant cell is by transformation of plant organelles (such as chloroplast or mitochondria), such as by particle bombardment. Although the plasmid will not replicate in the plant organelles, the exogenous DNA may be incorporated into the genome by recombination.

As used throughout this application, electroporation is a transformation method in which, generally, a high concentration of plasmid DNA (containing exogenous DNA) is added to a suspension of host cell protoplasts or bacterial cells and the mixture shocked with an electrical field of 200 to 600 V/cm. Following electroporation, transformed cells are identified by growth on appropriate medium containing a selective agent.

As also used throughout this application, particle bombardment (also know as biolistic transformation) of the host cell can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the exogenous DNA. Alternatively, the target cell can be surrounded by the plasmid so that the plasmid is carried into the cell by the wake of the particle. Biologically active particles (e.g., dried bacterial cells containing the plasmid and exogenous DNA) can also be propelled into plant cells.

Thus, the invention further provides a method of targeting a DNA molecule into the nucleus of a host cell. The method comprises providing a plasmid (the plasmid comprising the sequence of the nuclear targeting molecule or protein and the DNA molecule to be targeted) and introducing the plasmid into the cytoplasm of the host cell, or providing a nuclear targeting protein complexed to the DNA molecule to be targeted. In this method, the nuclear targeting molecule or protein targets the DNA molecule into the nucleus of the host cell.

Further provided is a purified nuclear targeting peptide of a VirE2 protein of Agrobacterium, the nuclear targeting peptide of the VirE2 protein having a mutation therein which renders the nuclear targeting peptide of the VirE2 protein capable of targeting deoxyribonucleic acid into the nucleus of an animal cell. In one presently preferred embodiment, the mutation comprises one or more amino acid subsitutions in the nuclear targeting peptide having SEQ ID NO:1. More particularly, the mutated nuclear targeting peptide of a VirE2 protein is designated VirE2s11 and the one or more substitutions comprise a substitution of arginine for leucine and leucine for arginine to produce SEQ ID NO:2. In another presently preferred embodiment, the mutation comprises one or more amino acid substitutions in the nuclear targeting peptide having SEQ ID NO:3. More particularly, the mutated nuclear targeting peptide of a VirE2 protein is designated VirE2s20 and the one or more substitutions comprise a substitution of threonine for lysine and lysine for threonine to produce SEQ ID NO:4.

In accordance with the subject invention as described above, Agrobacterium T-DNA nuclear transport was used to examine (i) the specificity of nuclear targeting between plants and animals, and (ii) the nuclear import of DNA by a specialized transport protein. Two karyophilic Agrobacterium proteins, VirD2 and VirE2, which presumably associate with the transported T-DNA and function in many plant species, were microinjected into Drosophila embryos and Xenopus oocytes. In both animal systems, VirD2 localized to the cell nuclei and VirE2 remained exclusively cytoplasmic, suggesting that VirE2 nuclear localization signals (NLSs) may be plant-specific.

To overcome this difficultly, a VirE2 derivative, VirE2s20, was constructed in which a single amino acid residue was repositioned within the NLS sequence. This mutant protein efficiently accumulated in the nuclei of Drosophila embryos and Xenopus oocytes. Furthermore, VirE2s20 was able to form complexes with ssDNA and actively transport them into the nucleus of Xenopus oocyte cells. The VirE2s20-ssDNA complexes can be used as a system to increase the efficiency of expression of foreign DNA and can be used for the production of transgenic organisms with homogenous rather than mosaic patterns of gene expression. Nuclear targeting of DNA can also enhance the current gene therapy techniques. Specifically, most DNA molecules introduced into the target cells (usually, by liposome fusion) do not reach the nucleus. Encapsulation of VirE2s20 bound to the DNA of interest into liposomes followed by fusion with the target cell membrane can improve expression of the transfected gene.

The invention thus provides an efficient system for targeting the DNA of interest (gene) into the nucleus of cells. Improved nuclear delivery of genes is expected to enhance the current techniques for gene therapy and production of transgenic organisms with homogenous rather than mosaic patterns of gene expression. This system utilizes a protein that strongly associates with the transported DNA molecule and actively guides it into the cell nucleus.

Materials and Methods

Protein Purification

VirD2 and VirE2 were produced in *Escherichia coli* strain BL21(DE3)pLysE with the T7 RNA polymerase expression system (Studier et al. 1990). The proteins were expressed as fusions with the first 11 amino acids of the gene 10 protein of the pET3 vector (Studier et al. 1990) as described (Citovsky et al. 1989; Howard et al. 1989) and purified as described for purification of the gene I protein of cauliflower mosaic virus (Citovsky et al. 1991). The VirE2s11 and VirE2s20 mutants of VirE2 were constructed by oligonucleotide-directed mutagenesis (McClary et al. 1989). The mutant proteins were then produced, purified and fluorescently-labeled as described for the wild-type VirE2.

Fluorescent Labeling of Proteins

Protein solutions (2–4 mg/ml) in 10 mM HEPES pH 7.5, 100 mM NaCl, 10% glycerol (buffer H) were mixed in a 1:25 (w/w) ratio with tetramethylrhodamine-5-(and-6-)-maleimide (Molecular Probes, Inc., USA) and incubated for 2 hours at room temperature in the dark. Following incubation, the labeled proteins were separated on SDS polyacrylamide gels and electroeluted as described (Citovsky et al. 1989); this procedure resulted in greater than 95% pure and biologically active protein preparations (Citovsky et al. 1989). The fluorescently-labeled proteins were adjusted to the 4 mg/ml concentration, aliquoted and stored at −70° C. until use.

Fluorescent Labeling of DNA

Fluorescent DNA was obtained by PCR amplification of an unrelated DNA fragment [a 717 bp promoterless sequence of the *Aequorea victoria* green fluorescent protein, GFP, gene (Chalfie et al. 1994)]. The reaction was performed using the Deep Vent DNA polymerase (New England Biolabs) in the presence of 0.4 mM dATP, dCTP and dGTP, 0.3 mM dTTP and 0.02 mM of rhodamine-conjugated dUTP (Boehringer-Mannheim). After 32 cycles of amplification (2 minutes at 94° C., 5 minutes at 55° C., and 3 minutes at 72° C.), the labeled DNA was separated from the unincorporated label on NucTrap push-columns (Stratagene).

Formation of Protein-ssDNA Complexes

Fluorescently-labeled DNA (1 μl of 1 mg/ml solution) was denatured for 5 minutes at 95° C. in a Perkin Elmer GeneAmp PCR System 2400 thermocycler. The resulting ssDNA was incubated for 10 minutes at 4° C. with saturating amounts (10 μg) of unlabeled VirE2 or VirE2s20 proteins and the protein-ssDNA complexes were immediately injected into Xenopus oocytes.

Gel Mobility Shift Assay

The indicated amounts of the purified VirE2, VirE2s11, or VirE2s20 proteins were incubated for 10 minutes at 4° C. in 20 μl of buffer H with 0.025 μg of the end-labeled ssDNA [717 bp fragment of the GFP DNA (Chalfie et al. 1994)]; to produce ssDNA, the radioactively-labeled probe was denatured for 5 minutes at 95° C. Following incubation, protein-ssDNA complexes were resolved on a 4% native polyacrylamide gel as described (Citovsky et al. 1989).

Microinjection of Drosophila Embryos

Drosophila embryos were dechorionated, affixed to a coverslip, and air-dried for 5–7 minutes. The coverslips were then transferred to the stage of an inverted microscope and the embryos were microinjected with fluorescently-labeled protein. The distribution of the label within the microinjected embryos was monitored using a Bio-Rad MRC 600 laser scanning confocal attachment and a Nikon Diaphot inverted microscope.

The fluorescent staining patterns analyzed represented at least four independent experiments; in each experiment, 10 to 20 individual Drosophila embryos or Xenopus oocytes (see below) were microinjected and the images were recorded 30 minutes after injection (except for the kinetic experiments where the nuclear import was recorded at 1 minute intervals). In co-injection experiments, the concentration of unlabeled synthetic peptides corresponding to the VirD2 NLS and VirE2 NSE2 sequences was 5 mg/ml (co-injection with VirD2) or 4 mg/ml (co-injection with VirE2 and VirE2s20). These concentrations corresponded to approximately 30-fold molar excess of peptide in 1:1 (v/v) peptide to protein co-injection mixture. The amino acid sequence of VirD2 NLS and VirE2 NSE2 is shown in Table 1.

Microinjection of Xenopus Oocytes

Full-grown Xenopus oocytes (stage VI) were obtained and microinjected with rhodamine-labeled protein into the cytoplasm at the equator of the oocyte or into the nucleus as described (Kay 1991). Thirty minutes after injection of rhodamine-labeled proteins, DNA or DNA-protein complexes, oocytes were fixed in methanol, cleared with benzyl benzoate:benzyl alcohol (2:1) and viewed under a confocal microscope as described for Drosophila embryos. For isolation of the cell nuclei, the fixed and cleared oocytes were processed as described (Gall and Murphy 1991).

EXAMPLE I

Nuclear Import of VirD2 in Drosophila Embryos

VirD2 and VirE2 were used to determine whether their NLSs are able to function in evolutionarily-distant animal cells. To this end, VirD2 and VirE2 were produced in *Escherichia coli* and purified to near homogeneity. The purified proteins were fluorescently tagged at cysteine residues; the cysteine-specific labeling (Haugland 1994) avoids modification of basic residues critical for the NLS activity. The fluorescent proteins were then microinjected into 1.5–2 hour-old Drosophila embryos. At this developmental stage, Drosophila embryos contain 750 to 6000 nuclei in a syncytium (no individual cell membranes); most of these nuclei are at the embryo surface and easily visualized (reviewed by Campos-Ortega and Hartenstein 1985). Following microinjection, rhodamine-labeled VirD2 accumulated in Drosophila nuclei. This nuclear import was very efficient, since virtually all observed nuclei took up the label. The nuclear location of the fluorescent protein was confirmed by costaining with the DNA binding dye oligreen (Haugland 1994).

Next, a test was done to determine whether the nuclear accumulation of the label reflected an active process of nuclear import. Since such process always requires NLS (reviewed by Garcia-Bustos et al. 1991; Forbes 1992), it should be specifically inhibited by competing amounts of the free signal peptide which presumably saturates the nuclear import machinery (Michaud and Goldfarb 1991; Guilizia et al. 1994). VirD2 was coinjected with a 30-fold molar excess of a synthetic peptide corresponding to the VirD2 NLS. VirD2 nuclear import was completely blocked by this peptide. Furthermore, VirD2 nuclear uptake was also inhibited by co-injection of a non-hydrolyzable analog of GTP (GTPγS). GTPγS has been shown to block the Ran/TC4 GTPase which is absolutely essential for the transport of proteins through the nuclear pore complex (Melchior 1993; Moore and Blobel 1993; Goldfarb 1994). Collectively, these results indicate that VirD2 is actively imported into the nuclei of Drosophila embryos and that this import is specifically mediated by the VirD2 NLS.

To further characterize the dynamics of VirD2 nuclear import in Drosophila, the microinjected embryos were recorded using time-lapse video microscopy. The VirD2 fluorescence intensity within each of twenty randomly-chosen nuclei was monitored from the moment of injection. The kinetics of VirD2 nuclear import were determined by comparing the amount of fluorescence in the cytoplasm to that in the individual nuclei at different time periods. These experiments showed that practically all of the injected VirD2 accumulated in the Drosophila nuclei within 10 minutes after microinjection (FIG. 1). This time-course of the VirD2 nuclear import is comparable to that reported for animal NLS-containing proteins (Rihs and Peters 1989; Rihs et al. 1991). Thus, the results establish that the plant NLS residing in the VirD2 protein is active in an animal system.

EXAMPLE II

VirE2 remains Cytoplasmic in Drosophila Embryos

VirD2 is a minor component of the T-complex compared to VirE2. For example, a nopaline-type Agrobacterium is thought to produce a T-complex containing only one molecule of VirD2 and about 600 molecules of VirE2 (reviewed by Citovsky and Zambryski 1993). Deletion of the VirD2 NLS only partially inhibits Agrobacterium tumorigenicity (Shurvinton et al. 1992), suggesting an important role for VirE2 in this process; consistent with these observations, VirE2 efficiently accumulates in the cell nuclei in various plant species (Citovsky et al. 1992b; Citovsky et al. 1994). To test whether this protein also functions in animal cells, fluorescently-labeled VirE2 was used to assay the activity of its NLSs in Drosophila embryos. Surprisingly, VirE2 remained cytoplasmic in Drosophila. This complete absence of nuclear import demonstrates that the VirE2 NLSs are not recognized in this animal system.

EXAMPLE III

Single Amino Acid changes in NLSs of VirE2 promote its Nuclear Import in Drosophila Embryos To determine the molecular basis for the functional difference between the VirD2 and VirE2 NLSs, the amino acid sequence of both VirE2 NLSs was compared to the VirD2 NLS and to the NLS of Xenopus nucleoplasmin (Robbins et al. 1991), a paradigm for the bipartite NLS sequence found in the large majority of nuclear-targeted proteins (Dingwall and Laskey 1991). Table 1 shows that while VirD2 and VirE2 NLSs are generally homologous to the bipartite NLS of nucleoplasmin, the similarity of the VirD2 NLS to nucleoplasmin is greater than that of the VirE2 NLSs. Specifically, bipartite NLSs are composed of two basic domains separated by a variable-length spacer (usually 9 to 11 residues). The first domain contains two adjacent basic amino acid residues, and the second domain contains five residues, three of which are basic (Dingwall and Laskey 1991; Robbins et al. 1991). As shown in Table 1, the VirD2 NLS (Howard et al. 1992) perfectly fits the bipartite motif. In contrast, the VirE2 NLSs [previously designated NSE1 and NSE2 (Citovsky et al. 1992b)] have a consensus-type second domain but differ in their first domains. Both NSE1 and NSE2 have an uncharged amino acid residue positioned between the two basic residues of the first domain (Table 1). It is possible that this single amino acid deviation from the consensus motif underlies the inability of the VirE2 NLSs to function in Drosophila, rendering it unrecognizable by the Drosophila nuclear import machinery. To test this idea, VirE2 mutants were produced in which the intervening uncharged amino acid residue was switched with the adjacent basic residue of the first domain. Specifically, the leucine residue of NSE1 was switched with the adjacent arginine, changing the first domain sequence from KLR to KRL (mutant VirE2s11, Table 1), and the threonine residue of NSE2 was switched with the adjacent lysine, changing the first domain from KTK to KKT (mutant VirE2s20, Table 1). The VirE2s11 and VirE2s20 mutant proteins were then fluorescently-labeled and microinjected into Drosophila embryos. The results showed that both VirE2s11 and VirE2s20 efficiently localized to the Drosophila nuclei.

While the imported VirD2 was randomly distributed within the Drosophila nuclei, the s11 and s20 mutant versions of VirE2 accumulated in distinct subdomains inside the nuclei. Because VirE2 is a sequence-nonspecific SSB (Gietl et al. 1987; Christie et al. 1988; Citovsky et al. 1988; Citovsky et al. 1989) and most SSBs also bind RNA and double-stranded DNA with low affinity (reviewed by Chase and Williams 1986), this staining pattern may represent the association of VirE2 with the nuclear DNA and/or RNA. In contrast, VirD2 should not bind nucleic acids since its association with DNA is limited to a specific 25 bp sequence found in the T-DNA borders (reviewed by Zambryski et al. 1989; Citovsky et al. 1992a; Zambryski 1992).

It is important to note that all of the microscopic data were confocal optical sections with the plane of focus through the cell nuclei. Thus, the fluorescent staining of the Drosophila nuclei following microinjection of VirD2, VirE2s11, and VirE2s20 reflected protein accumulation within the nuclei, rather than simply binding to the outer surface of the nuclear envelope.

EXAMPLE IV

Probing the Specificity of Nuclear Import by Competition with Synthetic NLS Peptides Synthetic NLS peptides co-injected with a nuclear-targeted protein inhibit its nuclear transport presumably by competing for the NLS-binding receptor (Michaud and Goldfarb 1991; Guilizia et al. 1994). Thus, these peptides can be used to assay for the presence of cellular receptors recognizing specific NLS sequences; only peptides that compete for the same receptor as the tested NLS will inhibit its import into the nucleus.

This approach was used to support the idea that VirD2 but not VirE2 NLSs function in Drosophila. A synthetic peptide corresponding to the second VirE2 NLS [NSE2 (Citovsky et al. 1992b)] was coinjected with the rhodamine-labeled VirD2. This peptide failed to inhibit nuclear import of VirD2. The co-injected NSE2 peptide also did not affect nuclear accumulation of VirE2s20. These results indicate that the VirE2 NLS is not recognized by the Drosophila nuclear transport machinery. In contrast, the VirD2 NLS peptide efficiently inhibited nuclear transport of both VirD2 and VirE2s20.

EXAMPLE V

Nuclear Import of VirD2 and VirE2 in Xenopus Oocytes

The results indicate that the NLS signals of VirE2 do not function in animal cells and, thus, may be plant-specific. To determine the generality of this observation, the nuclear transport of VirE2 and VirE2s20 was tested in an unrelated animal system, Xenopus oocytes. VirD2 was efficiently transported into the cell nucleus following microinjection into the cytoplasm of a Xenopus oocyte. Similarly efficient nuclear import was observed with the VirE2s20 protein while the wild-type VirE2 was excluded from the nucleus and remained cytoplasmic. The position of the nucleus in these experiments was confirmed using the chromatin-specific stain 4',6-diamidino-2-phenylindole (DAPI).

EXAMPLE VI

The VirE2s20 Protein Delivers DNA into the Nuclei of Xenopus Oocytes

Because VirE2 is both a nuclear-targeted protein and an SSB, it may function to transport ssDNA into the cell nucleus. This hypothesis was directly tested. First, the ssDNA binding of the wild-type VirE2 protein and its s11 and s20 derivatives was assayed. The SSB activity of VirE2s11 was lower than that of the wild-type VirE2, confirming earlier observations that VirE2 NLSs partially overlap its ssDNA binding site (Citovsky et al. 1992b; Citovsky et al. 1994). In contrast, the SSB activity of VirE2s20 was indistinguishable from that of the wild-type protein. Both VirE2 and VirE2s20 saturated the ssDNA probe at approximately 10:1 w/w ratio, consistent with previous characterization of the wild-type VirE2 protein (Citovsky et al. 1989). These results suggest that the s11 mutation may have caused some conformational changes in VirE2 while the s20 mutation likely did not interfere with the protein conformation.

Based on these observations, VirE2s20 was used to test its ability to transport ssDNA into the cell nucleus. To this end, ssDNA was mixed in vitro with the purified VirE2s20 to form VirE2s20-ssDNA complexes. Because such complexes are large [approximately $2.5 \times 10^6$ daltons per 1 kb of DNA (Citovsky and Zambryski 1993)], they frequently clog microinjection needles. To circumvent this technical difficulty, VirE2s20-ssDNA complexes were microinjected into Xenopus oocytes; microinjection into these cells allows the use of relatively wide needle bores. The nuclear import of VirE2s20-ssDNA complexes was assayed directly using fluorescently-labeled DNA. The results showed that the fluorescent ssDNA alone did not enter the cell nucleus following microinjection into the oocyte cytoplasm. Under the same conditions, VirE2s20-ssDNA complexes were efficiently imported into the oocyte nucleus. Nuclear accumulation of the fluorescent ssDNA complexed with VirE2s20 was similar to that achieved by microinjecting the ssDNA alone into the oocyte nucleus. The position of the nucleus in oocyte cells was confirmed by cytoplasmic microinjections of the chromatin-specific stain DAPI.

VirE2s20-mediated nuclear import of ssDNA was further confirmed using the nuclei isolated from the microinjected oocytes. When the nuclei from the oocytes injected with the fluorescent VirE2s20-ssDNA complexes were removed and directly examined under a confocal microscope, they contained the fluorescent signal. In contrast, the nuclei from cells microinjected with the fluorescent ssDNA alone displayed no fluorescence above the background level. The nuclear import of VirE2s20-ssDNA complexes was inhibited by co-injection of the synthetic VirD2 NLS peptide. These results demonstrate that the VirE2s20 mutant protein is able to transport ssDNA into the cell nucleus and that this transport likely occurs by a protein NLS-dependent pathway.

Finally, a determination was made of whether physical association between an NLS-containing protein and DNA is required for the DNA nuclear import. Agrobacterium VirD2 was used as an example of nuclear-targeted protein that does not bind DNA. Similarly to VirE2s20, VirD2 has a functional consensus bipartite NLS (Table 1) and efficiently localizes to the animal cell nuclei. Unlike VirE2s20, however, VirD2 binding to DNA is highly specific and is limited to the double-stranded 25 bp sequence of the T-DNA borders (reviewed by Zambryski et al. 1989; Citovsky et al. 1992a; Zambryski 1992). Thus, VirD2 is not expected to form complexes with the fluorescently-labeled ssDNA probe which does not contain these borders. When this fluorescent ssDNA was mixed with VirD2 and microinjected into the oocyte cytoplasm, the DNA remained exclusively cytoplasmic. This observation suggests that DNA molecules must be complexed with the transport protein (such as VirE2s20) to enter the nucleus.

EXAMPLE VII

While the function and structure of protein NLSs have bene extensively studied in practically all eukaryotic systems, the possibility of NLS specificity between animals and plants had not been examined. Another long-standing question is whether a specific NLS-containing protein can directly mediate nuclear import of DNA molecules. Here, the nuclear import of Agrobacterium VirD2 and VirE2 was used as an experimental system to address these questions. The results provide evidence for two functional types of plant NLSs: (i) a general type, exemplified by the VirD2 NLS which is active both in plant and animal systems, and (ii) a potentially plant-specific NLS, such as the NSE1 and NSE2 signals of VirE2, which are active in many plant species but non-functional in animal systems. Structurally, the VirD2 general NLS precisely conforms to the bipartite NLS sequence as defined for Xenopus nucleoplasmin (Dingwall and Laskey 1991; Robbins et al. 1991); in contrast, the VirE2 NLS deviates from the bipartite NLS in its first domain. Interestingly, both VirE2 NLSs differ from the VirD2 NLS and from the bipartite consensus in the position of only one amino acid. The results herein indicate that one uncharged amino acid residue positioned between two basic residues of the first bipartite domain does not interfere with the NLS function in plant cells (Citovsky et al. 1992b; Citovsky et al. 1994), but completely blocks the NLS activity in animal systems. Repositioning of this intervening amino acid outside the first bipartite domain converts the VirE2 NLS into the general type, active both in plant and animal systems.

The DNA transport function of VirE2 was demonstrated using microinjection of in vitro-formed complexes between ssDNA and purified VirE2s20. The results show that free DNA molecules microinjected into the oocyte cytoplasm do not enter the cell nucleus. They accumulate in the nucleus only when complexed with VirE2s20, a nuclear-targeted SSB. The VirE2s20-ssDNA complexes are likely imported into the cell nucleus via a protein-specific pathway because this import was inhibited by the excess of a synthetic bipartite NLS peptide. VirD2 which also contains NLS but does not bind ssDNA did not promote nuclear import, indicating that the NLS signals must be physically associated with the transported DNA molecule. While the NLS signals of VirE2 may be plant-specific, its biological function, i.e. nuclear transport of DNA, is not. Thus, the DNA nuclear import by formation of complexes between DNA and a specialized transport protein(s) may be relevant to many eukaryotic organisms. In addition, VirE2s20 may be used to efficiently deliver DNA into the cell nuclei, thereby improving the rate of transformation and producing homogenous rather than mosaic patterns of gene expression. The model for protein-mediated nuclear import of nucleic acids is supported by the recent observations that (i) influenza virus nucleoprotein transports the viral genomic RNA into the cell nucleus in an in vitro system (O'Neill et al. 1995), and (ii) the wild-type VirE2 actively transports ssDNA into the nucleus of the stamen hair cells of Tradescantia (Zupan et al. 1996).

EXAMPLE VIII

VirE2s20-ssDNA complexes constructed in vitro were also introduced into yeast cells. Because yeast cells are susceptible to Agrobacterium infection (Piers et al. 1996), they are a good choice for initially assessing the ability of VirE2 to mediate functional transport of DNA into the cell nucleus. Due to potential artifacts associated with very high frequency of homologous recombination in yeast cells, circular DNA molecules were used which do not integrate.

A yeast strain harboring a high copy number plasmid (pSJ101/VirE2s20, $2\mu$) which expresses the VirE2s20 protein was produced. VirE2s20 production was induced by addition of galactose and allowed to proceed for 6 hours. At that time, cells were harvested and prepared for electroporation.

An Agrobacterium gene encoding the VirD2 protein under the control of yeast Gal4 promoter was subclonsed into a bacterial plasmid pUC118. A single-stranded copy of this construct was produced in *E. coli* following infection with a helper M13K07 phage. This ssDNA was then electroporated into the yeast cells which have expressed VirE2s20. The VirD2 protein was chosen as an expression reporter because it has a functional NLS signal and accumulates in the cell nucleus, thereby increasing its local concentration and facilitating detection.

Following 4 hours of expression, the cells were processed for immunofluorescence microscopy and the presence of VirD2 was examined using affinity-purified anti-VirD2 antibody. When the VirD2 gene was transfected into VirE2s20-expressing yeast cells, the VirD2 protein was detected in many cell nuclei. The position of the nucleus was confirmed by chromatin-specific DAPI staining. In contrast, electroporation of the VirD2 gene into control yeast cells did not result in expression, producing only the background immunofluorescence. These results suggest that the presence of VirE2s20 facilitated expression of the transfected single-stranded copy of the VirE2 gene, by mediating its import into the recipient cell nucleus.

For a more quantitative analysis of expression, ssDNA containing the bacterial β-galactosidase (lacZ) gene under the Gal4 promoter was electroporated into yeast cells expressing VirE2s20. β-galactosidase enzymatic activity in yeast extracts was determined using o-nitrophenyl β-D-galactoside as substrate. The measurements were performed as described (Herrera-Estrella et al. 1990). The results are shown in Table 2, and support the conclusion that VirE2s20 can be used to enhance transient expression of foreign genes by facilitating nuclear import of the transfected DNA molecules.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

|  | first domain | second domain |
| --- | --- | --- |
| wt VirE2 NSE1 | Kl Rpedryiqte- | KygRR (SEQ ID NO: 1) |
| s11 | KR l••••••••- | KygRR (SEQ ID NO: 2) |
| wt VirE2 NSE2 | Kt Kygsdtei--- | KlKsK (SEQ ID NO: 3) |
| s20 | KK t•••••••--- | KlKsK (SEQ ID NO: 4) |
| VirD2 | KR predddgepse | RKReR (SEQ ID NO: 5) |
| nucleoplasmin | KR paatkkagqa- | KKKKl (SEQ ID NO: 6) |

TABLE 2

| Cells Expressing | Transformed With | β-gal activity (units)[a] |
| --- | --- | --- |
| VirE2s20 | ss copy of lacZ | 877.62 |
| VirE2s20 | — | 0.0 |
| — | ss copy of lacZ | 33.85 |

[a] one unit of enzyme was defined to produce 1 nmol of nitrophenol per mg of protein per minute

LIST OF REFERENCES CITED

Baru, M., et al., Gene 161(2):143–150 (1995).
Betz, A. L., et al., J Cereb Blood Flow Metab 15(4):547–551 (1995).
Brownlee, G. G., Br Med Bull 51(1):91–105 (1995).
Bukrinsky, M. I., et al., *Nature* 365:666–669 (1993).
Bukrinsky, M. I., et al., *Proc Natl Acad Sci USA* 89:6580–6584 (1992).
Campos-Ortega, J. A., and Hartenstein, V., *The embryonic development of Drosophila melanogaster*, Berlin Heidelberg: Springer Verlag, p. 227 (1985).
Capecchi, M., Cell 22:479–488 (1980).
Chalfie, M., et al., Science 263:802–805 (1994).
Chase, J. W., and Williams, K. R., Annu Rev Biochem 55:103–136 (1986).
Christie, P. J., et al., J Bacteriol 170:2659–2667 (1988).
Citovsky, V., et al., Science 240:501–504 (1988).
Citovsky, V., et al., Proc Natl Acad Sci USA 88:2476–2480 (1991).
Citovsky, V., et al., In: *Molecular Signals in Plant-Microbe Communications*, D.P.S. Verma, ed., CRC Press, Inc., p. 169–198 (1992a).
Citovsky, V., et al., Proc Natl Acad Sci USA 91:3210–3214 (1994).
Citovsky, V., et al., Proc Natl Acad Sci USA 86:1193–1197 (1989).
Citovsky, V., and Zambryski, P., Annu Rev Microbiol 47:167–197 (1993).
Citovsky, V., and Zambryski, P., Membr Prot Transport 1:39–57 (1995).
Citovsky, V., et al., Science 256:1803–1805 (1992b).
Clever, J., et al., Proc Natl Acad Sci USA 88:7333–7337 (1991).
Dingwall, C., and Laskey, R. A., Trends Biochem Sci 16:478–481 (1991).
Dowty, M. E., et al., *Proc Natl Acad Sci USA* 92:4572–4576 (1995).
Ekhterae, D. and J. C. Stanley, J Vasc Surg 21(6):953–962 (1995).
Escudero, J., et al., *Proc Natl Acad Sci USA* 92:230–234 (1995).
Fields, B. N., et al., Eds., *Virology*, Raven Press, New York (1990).
Finlay, D. R., et al., *J Cell Biol* 104:189–200 (1987).
Forbes, D. J., Annu Rev Cell Biol 8:495–527 (1992).
Gall, J. G., and Murphy, C., Methods Cell Biol 36:149–166 (1991).
Garcia-Bustos, J., et al., Biochim Biophys Acta 1071:83–101 (1991).
Gietl, C., et al., Proc Natl Acad Sci USA 84:9006–9010 (1987).
Goldfarb, D., Curr Biol 4:57–60 (1994).
Guilizia, J., et al., J Virol 68:2021–2025 (1994).
Hamm, J., et al., Cell 62:569–577 (1990).
Haugland, R. P., *Molecular probes: handbook of fluorescent probes and research chemicals*, Eugene, Oreg.: Molecular Probes, Inc., p. 1–19 (1994).
Herrera-Estrella, A., et al., EMBO J 7:4055–4062 (1988).
Herrera-Estrella, A., et al., Proc Natl Acad Sci USA 87:9534–9537 (1990).
Hicks, G. R. and N. V. Raikhel, *Annu Rev Cell Dev Biol* 11:155–188 (1995).
Hirooka, T., et al., J Bacteriol 169:1529–1536 (1987).
Howard, E., et al., Cell 68:109–118 (1992).
Howard, E. A., and Citovsky, V., BioEssays 12:103–108 (1990).
Howard, E. A., et al., UCLA Symp Mol Cell Biol New Ser 129:1–11 (1990).
Howard, E. A., et al., Proc Natl Acad Sci USA 86:4017–4021 (1989).
Kaneda, Y., et al., Science 243:375–378 (1989).
Kay, B. K., Methods Cell Biol 36:663–669 (1991).

Klein, T. M., et al., Nature 327:70–73 (1987).
Knowles, M. R., et al., N Engl J Med 333(13):823–831 (1995).
Kojima, H., et al., Biochem Biophys Res Commun 212(2):712–717 (1995).
Mannino, R. J. and Gould-Fogerite, S., BioTechniques 6:682–690 (1988).
McClary, J. A., et al., BioTechniques 7:282–289 (1989).
Melchior, F., et al., J Cell Biol 123:1649–1659 (1993).
Melchoir, F. and L. Gerace, Curr Opinion Cell Biol 7:310–318 (1995).
Michaud, N., and Goldfarb, D., J Cell Biol 112:215–223 (1991).
Michaud, N. and D. Goldfarb, J Cell Biol 116:851–861 (1992).
Miller, L. K., Bioessays 11:91–95 (1989).
Moore, M. S., and Blobel, G., Nature 365:661–663 (1993).
O'Neill, R. E., et al., J Biol Chem 270:22701–22704 (1995).
Osborne, W. R., et al., Proc Natl Acad Sci USA 92(17):8055–8058 (1995).
Phaneuf, D., et al., Biochem Biophys Res Comm 208(3):957–963 (1995).
Piers, K. L., et al., Proc Natl Acad Sci USA 93:1613–1618 (1996).
Rihs, H.-P., et al., EMBO J 10:633–639 (1991).
Rihs, H.-P., and Peters, R., EMBO J 8:1479–1484 (1989).
Robbins, J., et al., Cell 64:615–623 (1991).
Rowland, R. T., et al., Ann Thorac Surg 60(3):721–728 (1995).
Sambrook et al., *Molecular Cloning: A Laboratory Manual*, 2d Edition, Cold Spring Harbor Laboratory Press, Cold Spring Harbor, N.Y. (1989).
Shigekawa, K. and Dower, W. J., BioTechniques 6:742–751 (1988).
Shurvinton, C. E., et al., Proc Natl Acad Sci USA 89:11837–11841 (1992).
Stevenson, S. C., et al., Arterioscler Thromb Vasc Biol 15(4):479–484 (1995).
Studier, F. W., et al., Methods Enzymol 185:60–89 (1990).
Tinland, B., et al., Proc Natl Acad Sci USA 91:8000–8004 (1994).
Vallejos, et al., Genetics 112:93–105 (1986).
Vaulont, S., et al., Transgenic Res 4(4):247–255 (1995).
von Schwedler, U., et al., *Proc Natl Acad Sci USA* 91:6992–6996 (1994).
Vrionis, F. D., et al., J Neurosurg 83(4):698–704 (1995).
Ward, E., and Barnes, W., Science 242:927–930 (1988).
Young, C., and Nester, E. W., J Bacteriol 170:3367–3374 (1988).
Yusibov, V. M., et al., Proc Natl Acad Sci USA 91:2994–2998 (1994).
Zambryski, P., Annu Rev Plant Physiol Plant Molec Biol 43:465–490 (1992).
Zambryski, P., et al., Cell 56:193–201 (1989).
Zupan, J., et al., Proc Natl Acad Sci USA 93(6):2392–2397 (1996).
Zupan, J. R. and P. Zambryski, *Plant Physiol* 107:1041–1047 (1995).

What is claimed is:

1. A mutated nuclear targeting protein of Agrobacterium, the nuclear targeting protein being designated VirE2s20 and comprising an amino acid sequence as shown in SEQ ID NO:4.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 17 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:1:

```
Lys  Leu  Arg  Pro  Glu  Asp  Arg  Tyr  Ile  Gly  Thr  Glu  Lys  Tyr  Gly  Arg
1                  5                       10                      15

Arg
```

( 2 ) INFORMATION FOR SEQ ID NO:2:

( i ) SEQUENCE CHARACTERISTICS:
    ( A ) LENGTH: 17 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:2:

```
Lys  Arg  Leu  Pro  Glu  Asp  Arg  Tyr  Ile  Gly  Thr  Glu  Lys  Tyr  Gly  Arg
1                  5                       10                      15

Arg
```

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

```
Lys Thr Lys Tyr Gly Ser Asp Thr Glu Ile Lys Leu Lys Ser Lys
1               5                   10                  15
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

```
Lys Lys Thr Tyr Gly Ser Asp Thr Glu Ile Lys Leu Lys Ser Lys
1               5                   10                  15
```

(2) INFORMATION FOR SEQ ID NO:5:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

```
Lys Arg Pro Arg Glu Asp Asp Asp Gly Glu Pro Ser Glu Arg Lys Arg
1               5                   10                  15
Glu Arg
```

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

```
Lys Arg Pro Ala Ala Thr Lys Lys Ala Gly Gln Ala Lys Lys Lys Lys
1               5                   10                  15
Leu
```